US009233355B2

(12) United States Patent
Onishi

(10) Patent No.: US 9,233,355 B2
(45) Date of Patent: Jan. 12, 2016

(54) SEPARATING AGENT

(71) Applicant: DAICEL CORPORATION, Osaka-shi, Osaka (JP)

(72) Inventor: Takafumi Onishi, Himeji (JP)

(73) Assignee: DAICEL CORPORATION, Osaka-shi, Osaka (JP)

(*) Notice: Subject to any disclaimer, the term of this patent is extended or adjusted under 35 U.S.C. 154(b) by 0 days.

(21) Appl. No.: 14/400,744

(22) PCT Filed: May 23, 2013

(86) PCT No.: PCT/JP2013/064338
§ 371 (c)(1),
(2) Date: Nov. 12, 2014

(87) PCT Pub. No.: WO2013/176215
PCT Pub. Date: Nov. 28, 2013

(65) Prior Publication Data
US 2015/0209757 A1 Jul. 30, 2015

(30) Foreign Application Priority Data

May 23, 2012 (JP) ................................. 2012-117627

(51) Int. Cl.
| | |
|---|---|
| *B01J 20/26* | (2006.01) |
| *B01J 20/29* | (2006.01) |
| *B01J 20/24* | (2006.01) |
| *B01J 20/283* | (2006.01) |
| *B01J 20/285* | (2006.01) |
| *B01J 20/10* | (2006.01) |
| *B01J 20/28* | (2006.01) |
| *C12Q 1/68* | (2006.01) |
| *C12N 15/09* | (2006.01) |
| *G01N 30/88* | (2006.01) |
| *B01J 20/286* | (2006.01) |
| *B01J 20/32* | (2006.01) |
| *C07K 1/16* | (2006.01) |

(52) U.S. Cl.
CPC ............... *B01J 20/29* (2013.01); *B01J 20/103* (2013.01); *B01J 20/24* (2013.01); *B01J 20/26* (2013.01); *B01J 20/283* (2013.01); *B01J 20/285* (2013.01); *B01J 20/286* (2013.01); *B01J 20/28016* (2013.01); *B01J 20/28083* (2013.01); *B01J 20/327* (2013.01); *B01J 20/3272* (2013.01); *B01J 20/3274* (2013.01); *C07K 1/16* (2013.01); *C12N 15/09* (2013.01); *C12Q 1/68* (2013.01); *G01N 30/88* (2013.01); *B01J 2220/54* (2013.01)

(58) Field of Classification Search
CPC ....................................................... B01J 20/26
USPC ....................................................... 502/402
See application file for complete search history.

(56) References Cited

U.S. PATENT DOCUMENTS

| | | | |
|---|---|---|---|
| 3,922,392 | A | 11/1975 | Kohlschütter et al. |
| 2003/0186298 | A1 | 10/2003 | Nishimura et al. |
| 2004/0077812 | A1 | 4/2004 | Okamoto et al. |
| 2005/0181441 | A1 | 8/2005 | Nishimura et al. |
| 2007/0189944 | A1 | 8/2007 | Kirkland et al. |
| 2010/0041878 | A1 | 2/2010 | Ohnishi et al. |
| 2010/0203646 | A1 | 8/2010 | Larsen et al. |
| 2011/0226990 | A1 | 9/2011 | Glennon et al. |

FOREIGN PATENT DOCUMENTS

| | | |
|---|---|---|
| JP | S49-036396 A | 4/1974 |
| JP | 04-077737 B2 | 12/1992 |
| JP | 10-128089 A | 5/1998 |
| JP | 11-335306 A | 12/1999 |
| JP | 2003-284552 A | 10/2003 |
| JP | 2003-327675 A | 11/2003 |
| JP | 2009-091535 A | 4/2009 |
| JP | 2010-077022 A | 4/2010 |
| JP | 2010-530345 A | 9/2010 |
| JP | 2012-018135 A | 1/2012 |
| JP | 2012-509974 A | 4/2012 |
| WO | WO02/088204 A1 | 11/2002 |
| WO | WO2008/102920 A1 | 8/2008 |

OTHER PUBLICATIONS

International Search Report for PCT/JP2013/064338 (1 page).
Comparative high-performance liquid chromatography enantioseparations on polysaccharide based chiral stationary phases prepared by coating totally porous and core-shell silica particles, by K. Lomsadze et al, Journal of Chromatography A, vol. 1234, 2012, pp. 50-55.
Chloromethylphenylcarbamate derivatives of cellulose as chiral stationary phases for high-performance liquid chromatography, by B. Chankvetadze et al, Journal of Chromatography A, vol. 670, 1994, pp. 39-49.
Chromatographic Resolution, XI* Controlled Chiral Recognition of Cellulose Triphenylcarbamate Derivatives Supported on Silica Gel, by Y. Okamoto et al, Journal of Chromatography, vol. 363, 1986, pp. 173-186.
Chromatographic Optical Resolution on 3,5-Disubstituted Phenylcarbamates of Cellulose and Amylose, by Y. Okamoto et al, Bull. Chem. Soc., Jpn., vol. 63, 1990, pp. 955-957.

(Continued)

*Primary Examiner* — Edward Johnson
(74) *Attorney, Agent, or Firm* — Flynn, Thiel, Boutell & Tanis, P.C.

(57) ABSTRACT

Provided is a novel separating agent obtained by using core/shell particles as a support and fixing any of various ligands to the support by physical adsorption. The separating agent contains a support and a ligand fixed to the surface of the support by physical adsorption, and is characterized in that the support is core/shell particles each formed of a core constituted of a nonporous inorganic substance and a porous shell, the shell having a pore diameter of 30 nm or larger, the shell being constituted of a hydrolyzate of a polyalkoxysiloxane, and the ligand is an optically active polymer, an optically inactive polyester, a protein, or a nucleic acid.

8 Claims, No Drawings

(56) References Cited

OTHER PUBLICATIONS

Dimethyl-, dichloro- and chloromethylphenylcarbamates of amylose as chiral stationary phases for high-performance liquid chromatography, by B. Chankvetadze et al, Journal of Chromatography A, vol. 694, 1995, pp. 101-109.

Useful Chiral Stationary Phases for HPLC, Amylose Tris (3,5-dimethylphenylcarbamate) and Tris(3,5-dichlorophenylcarbamate) Supported on Silica Gel[1], by Y. Okamoto et al, Chemistry Letters, 1987, pp. 1857-1860.

English translation of International Preliminary Report on Patentability and Written Opinion of the International Searching Authority for PCT/JP2013/064338 (5 pgs.).

European Patent Office Search Report issued in Application No. 13 79 3161 dated Jul. 13, 2015 (7 pages).

SEPARATING AGENT

TECHNICAL FIELD

The present invention relates to a separating agent which contains a specific support and a specific ligand fixed to the surface of the support by physical adsorption.

BACKGROUND ART

In the industrial fields related to medicines, agrochemicals, and biochemicals, it is an extremely important problem to separate/purify a target substance to be produced, and methods using separating agents have been conventionally employed as techniques for such separation. Examples of principles on which a substance to be separated is separated using such separating agents include one in which affinity between a separating agent and a target substance is utilized, and one in which the optical activity of both a separating agent and a target substance is utilized.

Separating agents, in which wholly porous silica gel is used as a support and various ligands are fixed to the support in accordance with a target substance to be separated, are conventionally known as such separating agents.

Known as such a separating agent obtained using wholly porous silica gel as a support is, for example, a separating agent containing an optically active polymer fixed therein. In the case of using such a separating agent in which an optically active polymer is fixed to a support, optical resolution can be performed.

Having been reported as the optically active polymer are polysaccharide derivatives derived from polysaccharides such as cellulose (see, for example, patent document 1), optically active poly(meth)acrylamides (see, for example, patent document 2), optically active poly(amino acid)s (see, for example, patent document 3), and optically active polyamides (see, for example, patent documents 4 and 5).

Meanwhile, a separating agent for optical isomers is also known in which an optically active low-molecular-weight compound (e.g., a compound having a binaphthyl structure or crown ether structure) is bonded to a support by chemical bonding (see, for example, patent document 6).

Furthermore reported is a separating agent which contains, as a support, particles constituted of a synthetic polymer having a crosslinked structure and further contains, as a ligand fixed thereto, either a protein or a glycoprotein having a sugar chain (see, for example, patent document 7).

With respect to separating agents obtained by fixing a nucleic acid to a support, a technique in which DNA is immobilized to a glass substrate through chitosan is, for example, known (see, for example, patent document 8).

Moreover, with respect to chips for use in identifying ionic polymers, a technique in which DNA, RNA, or the like is fixed to a support such as glass is also known (see, for example, patent document 9).

Wholly porous silica gel has conventionally been used as a support to be used for fixing ligands thereto. Regarding this, also known besides such wholly porous particles are core/shell particles each including a nonporous core and a porous shell covering the outer surface thereof (see, for example, patent document 10). Also known is a separating agent for optical isomers which is obtained by fixing cellulose tris(4-chloro-3-methylphenylcarbamate) to such core/shell particles which have a pore diameter of 10 nm (for example, non-patent document 1).

Patent Document 1: WO 2008/102920
Patent Document 2: WO 02/088204
Patent Document 3: Japanese Patent Application Laid-open No. H10-128089
Patent Document 4: Japanese Patent Application Laid-open No. H11-335306
Patent Document 5: Japanese Patent Application Laid-open No. 2009-91535
Patent Document 6: Japanese Patent Application Laid-open No. 2003-327675
Patent Document 7: Japanese Patent Application Laid-open No. 2012-18135
Patent Document 8: Japanese Patent Application Laid-open No. 2010-77022
Patent Document 9: Japanese Patent Application Laid-open No. 2003-284552
Patent Document 10: Japanese Patent Application Laid-open No. S49-36396
Patent Document 11: Japanese Examined Patent Publication No. H4-077737
Non-patent document 1: K. Lomsadze, G. Jibuti, T. Farkas, B. Chankvetadze, J. Chromatogr. A 1234 (2012) 50
Non-patent document 2: B. Chankvetadze, E. Yashima, Y. Okamoto, J. Chromatogr. A 670 (1994) 39
Non-patent document 3: Y. Okamoto, M. Kawashima, K. Hatada, J. Chromatogr. 363 (1986) 173
Non-patent document 4: Y. Okamoto, R. Aburatani, K. Hatada, Bull. Chem. Soc. Jpn. 63 (1990) 955
Non-patent document 5: B. Chankvetadze, E. Yashima, Y. Okamoto, J. Chromatogr. A 694 (1995) 101
Non-patent document 6: Y. Okamoto, R. Aburatani, T. Fukumoto and K. Hatada, Chem Lett., (1987) 1857

DISCLOSURE OF THE INVENTION

The present invention provides a novel separating agent obtained by using core/shell particles as a support and fixing any of various ligands thereto by physical adsorption.

The present inventors have found that separating agents obtained by using, as a support for use in the separating agents, not wholly porous particles which have conventionally been used, such as silica gel, but core/shell particles each configured of a nonporous core and a porous shell and fixing various ligands to the core/shell particles are useful for the separation of various target substances.

Namely, the invention provides a separating agent containing a support and a ligand fixed to the surface of the support by physical adsorption, wherein the support is core/shell particles each formed of a core constituted of a nonporous inorganic substance and a porous shell, the shell having a pore diameter of 30 nm or larger, the shell being constituted of a hydrolyzate of a polyalkoxysiloxane, and the ligand is an optically active polymer, an optically inactive polyester, a protein, or a nucleic acid.

MODE FOR CARRYING OUT THE INVENTION

<Core/Shell Particles>

In the separating agent of the invention, use is made of core/shell particles each configured of a nonporous core and a porous shell covering the outer surface thereof. The shells of the core/shell particles have a pore diameter of 30 nm or larger.

Since the pore diameter of the shells of the core/shell particles is 30 nm or larger, it is expected that a substance serving as a ligand infiltrates into inner parts of the shells of the core/shell particles and contributes to satisfactory separation of a target substance.

The pore diameter of the shells of the core/shell particles can be determined by the mercury intrusion method.

The pore diameter thereof is usually 300 nm or smaller.

The mercury intrusion method is a method in which pressure is applied to make mercury penetrate into the open pores, and the diameter of each pore that is assumed to be cylindrical is calculated from the pressure value and the corresponding volume of the mercury which has penetrated, using the Washburn equation. JIS R1655 for molded ceramic objects can be applied.

The term "nonporous" used herein means that when the specific surface area ($m^2/g$) of the surface of the core particles determined by the BET method is expressed by A and the surface area ($m^2/g$) thereof per unit weight that can be calculated from the surface area ($4\pi r^2$, which is calculated from the particle radius r) determined from the particle diameter of the core particles is expressed by B, then the value of (A–B)/B× 100 is less than 20.

Meanwhile, the term "porous" used herein means that the specific surface area of the surface of the material, determined by the BET method, is 10 $mm^2/g$ or larger.

The thickness ratio of the cores to the shells of the core/shell particles is usually from 1:9 to 9:1. This ratio is preferably from 4:1 to 2:1 from the standpoint of ensuring the satisfactory property of separating a target substance. This ratio can be controlled by controlling the thickness of the shell layers of the core/shell particles as will be described later.

The term "thickness of a core" herein means the diameter of the core.

The material of the cores as a constituent component of the core/shell particles is an inorganic substance. Specific examples thereof include nonporous particles selected from materials represented by glasses, metals such as titanium and zirconium, oxides of these metals, and clay minerals such as bentonite and mica.

The particles serving as the material of the cores have a particle diameter of preferably 0.1 μm or larger, more preferably 0.5 μm or larger, especially preferably 1 μm or larger. Meanwhile, the particles to be used as the material of the cores have a particle diameter of preferably 200 μm or smaller, more preferably 100 μm or smaller, especially preferably 50 μm or smaller.

Normally used are core/shell particles having a particle diameter of 0.2 to 1,000 μm.

The material of the shells as a constituent component of the core/shell particles is obtained by partially hydrolyzing an alkoxysilane and further hydrolyzing the resultant polyalkoxysiloxane. Such material is preferred from the standpoint that the core/shell particles can be easily produced.

Preferred as the alkoxysilane are tetraalkoxysilanes. Preferred of these are tetramethoxylane, tetraethoxysilane, tetrapropoxysilane, and tetrabutoxysilane. Use of tetraethoxysilane is more preferred.

For production of the core/shell particles, Japanese Patent Application Laid-open No. S49-36396 can be referred to. Specifically, an alkoxysilane is first partially hydrolyzed to yield a polyalkoxysiloxane. The polyalkoxysiloxane thus obtained is dissolved in a solvent such as an ether, acetone, or dichloromethane to prepare a polyalkoxysiloxane solution. This solution is applied to particles serving as the cores, or the core particles are immersed in this solution. Thereafter, the solvent is removed to deposit a layer of the polyalkoxysiloxane as shells on the surface of the core particles. Subsequently, the deposited polyalkoxysiloxane is condensation-polymerized (hydrolyzed) in the presence of water. Thus, core/shell particles can be obtained.

The thickness of the shells as a constituent component of the core/shell particles can be controlled, as appropriate, in the range of 0.1 to 100 μm. An example of methods therefor is to regulate the viscosity of the alkoxysilane which becomes the shells. For example, in cases when shells having an increased thickness are to be formed, the viscosity of the alkoxysilane is lowered.

Examples of methods for controlling the specific surface area and pore diameter of the shells include a method in which the pH of the aqueous solution to be used when deposited shells are condensation-polymerized is regulated. For example, the pH of the aqueous solution is increased when a larger specific surface area and a larger pore diameter are to be obtained.

The term "thickness of a shell" herein means the value obtained by subtracting the diameter of the core from the diameter of the core/shell particle and dividing the obtained value by 2.

As the core/shell particles, "core/shell type silica gel" which is available on the market can be used. Such a commercial product has, in terms of catalog values, a pore diameter, specific surface area, and particle diameter in the ranges mentioned above. Among such commercial products, core/shell type silica gel in which the cores are constituted of a glass and the shells are constituted of silica gel (hydrolyzate of a polyalkoxysiloxane) can be used.

The core/shell particles to be used as the support of the separating agent of the invention may be subjected to a surface treatment. Examples of methods for the surface treatment include a method in which a silane coupling agent having an amino group, such as 3-aminopropyltriethoxysilane, is used.

<Ligand>

The term "ligand" used herein means a substance which is fixed to the core/shell particles serving as the support and which shows a physical affinity for the target substance to be separated or is capable of recognizing the asymmetry thereof.

1. Optically Active Polymer

Examples of the ligand usable in the separating agent of the invention contain optically active polymers. The term "optically active polymer" used herein means a polymer, a solution of which, when plane-polarized light is passed therethrough, has optical rotary activity that rotates the plane of polarization, i.e., chirality.

More specifically, the optically active polymer is obtained from a monomer having optical activity, or is obtained by polymerizing an optically inactive monomer using a polymerization catalyst which is optically active. The polymer has a molecular weight of 1,000 to 1,000,000.

1-(1) Polysaccharides or Derivatives Thereof

Examples of the optically active polymer serving as the ligand for use in the invention include polysaccharides or derivatives thereof. Examples of such polysaccharides include β-1,4-glucan (cellulose), α-1,4-glucan (amylose, amylopectin), α-1,6-glucan (dextran), β-1,6-glucan (pustulan), β-1,3-glucan (curdlan, schizophyllan), α-1,3-glucan, β-1,2-glucan (crown-gall polysaccharide), β-1,4-galactan, β-1,4-mannan, α-1,6-mannan, β-1,2-fructan (inulin), β-2,6-fractan (levan), β-1,4-xylan, β-1,3-xylan, β-1,4-chitosan, β-1,4-N-acetylchitosan (chitin), pullulan, agarose, alginic acid, α-cyclodextrin, β-cyclodextrin, γ-cyclodextrin, nigeran, and starch containing amylose.

Preferred of these are cellulose, amylose, β-1,4-chitosan, chitin, β-1,4-mannan, β-1,4-xylan, inulin, curdlan, pullulan, α-cyclodextrin, β-cyclodextrin, γ-cyclodextrin, nigeran, and the like, from which high-purity polysaccharides can be easily obtained. More preferred are cellulose, amylose, pullulan, and nigeran.

The number-average degree of polymerization (the average number of pyranose or furanose rings contained in one molecule) of each polysaccharide is preferably 5 or greater, more preferably 10 or greater. Although there is no particular upper limitation thereon, the number-average degree of polymerization thereof is preferably 1,000 or less from the standpoint of ease of handling, and is more preferably 5 to 1,000, even more preferably 10 to 1,000, especially preferably 10 to 500.

With respect to these polysaccharides, an ester derivative, carbamate derivative, or the like obtained by chemically modifying, for example, cellulose or amylose can be used as the ligand according to the invention.

Such polysaccharide derivatives are known to have a high optical resolution ability when used as a chiral fixing phase.

Specific examples of the ester derivative and carbamate derivative include the cellulose derivative described in Japanese Examined Patent Publication No. H4-42371, in which hydroxy groups of cellulose have been modified with a substituent formed by replacing part of the hydrogen atoms of the aromatic ring of phenyl carbamate with a halogen (fluorine or chlorine), and the cellulose derivative and amylose derivative described in Japanese Patent Application Laid-open No. 2005-315668, in which hydroxy groups of cellulose or amylose have been modified with a substituent formed by replacing part of the hydrogen atoms of the aromatic ring of phenyl carbamate with one or more fluorine atoms, alkyl groups, or alkoxy groups. These derivatives also are usable as the ligand according to the invention.

Examples of the substituent with which hydrogen atom(s) of the aromatic ring of such phenyl carbamate derivatives are replaced include a halogen alone, a combination of a halogen and an alkyl group, and an alkyl group alone. Preferred examples of the halogen in such case include chlorine. Examples of the alkyl group include ones having 1-3 carbon atoms, and methyl is especially preferred of these.

Of the above polysaccharides or derivatives thereof, it is especially preferred to use a polysaccharide derivative selected from those described above, from the standpoints of the ability to separate an optical isomer to be separated and of ease of fixation thereof to the core/shell particles.

The polysaccharide derivatives are not limited to those described above and other polysaccharide derivatives can be used as appropriate.

For fixing the polysaccharide or derivative thereof to core/shell particles by physical adsorption, use may be made of a method in which the core/shell particles are immersed in a solution including the polysaccharide or derivative thereof and a solvent and the solvent is thereafter distilled off. Thus, the polysaccharide or derivative can be physically adsorbed onto the core/shell particles.

It is preferable that the amount of the polysaccharide or derivative thereof to be fixed to the core/shell particles should be 1.0 to 25 parts by weight per 100 parts by weight of the separating agent.

1-(2) Poly(meth)acrylamides

In the invention, examples of the optically active polymer serving as the ligand include poly(meth)acrylamides. Among such poly(meth)acrylamides, poly(meth)acrylamide obtained by polymerizing a (meth)acrylamide which is represented by the following formula (I) and is optically active can be preferably used.

Examples of such polymerization reaction include radical polymerization in which a free-radical polymerization initiator such as AIBN (azobisisobutyronitrile) is used in the presence of a Lewis acid catalyst.

The Lewis acid used therein is desirably a metallic Lewis acid which is a metal salt (MX). Examples thereof include scandium triflate, yttrium triflate, magnesium bromide, hafnium chloride, ytterbium triflate, and lutetium triflate.

In the polymerization reaction, when (meth)acrylamide is liquid at normal temperature and normal pressure, it can be polymerized even under solvent-free conditions. In cases when the (meth)acrylamide is solid, any common organic solvent which has no radical-trapping effect can be used as a reaction solvent. More desirable are tetrahydrofuran, chloroform, methanol, and the like.

Other polymerization conditions can be controlled, as appropriate, with reference to WO 02/088204.

[Chem. 1]

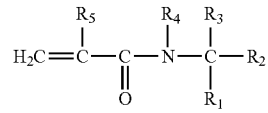

(I)

(In the formula, $R^1$, $R^2$, and $R^3$ are different and each represent a hydrogen atom, a monovalent hydrocarbon group having 1-30 carbon atoms, or a monovalent group of atoms including a heteroatom; $R^4$ represents a hydrogen atom or a monovalent hydrocarbon group having 1-30 carbon atoms; and $R^5$ represents a hydrogen atom or a methyl group.)

It is preferable that $R^1$, $R^2$, and $R^3$ be different and each be a hydrogen atom, alkyl group having 1-6 carbon atoms, aryl group, aralkyl group, carboalkoxy group, carbamoyl group, aminoalkyl group, amino group, alkoxyalkyl group, alkoxy group, or silyl group, and that $R^4$ be a hydrogen atom, alkyl group having 1-6 carbon atoms, aryl group, or aralkyl group. It is especially preferable that $R^4$ be a hydrogen atom.

It is preferable that the amount of the poly(meth)acrylamide to be fixed to the core/shell particles should be 1.0 to 25 parts by weight per 100 parts by weight of the separating agent.

For fixing the poly(meth)acrylamide in a core/shell particulate state by physical adsorption, use can be made of a method in which the core/shell particles are immersed in a solution of the poly(amino acid) (for example, chloroform or dichloromethane is used as the solvent) and the solvent is thereafter distilled off. Thus, the fixing is accomplished.

1-(3) Poly(Amino Acid)s

Examples of the optically active polymer for use in the invention include poly(amino acid)s. The term "poly(amino acid)s" used herein is not included in the proteins which will be described later. Examples of such poly(amino acid)s include ones represented by the following formula (II). Such poly(amino acid)s can be synthesized, for example, by the method described in Japanese Patent Application Laid-open No. S60-193538.

[Chem. 2]

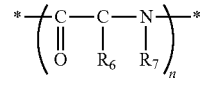

(II)

In formula (II), n is 5 or greater, and $R_6$ is a group selected from alkyl groups having 1-5 carbon atoms, a phenyl group, aralkyl groups having 7-12 carbon atoms, and heterocyclic groups. These groups may have a substituent such as a hydroxyl group, carboxyl group, mercapto group, amino group, or methylthio group. $R_7$ is an alkyl group having 1-5 carbon atoms, and is preferably a methyl or ethyl group.

Examples of heterocycles constituting the heterocyclic groups include 5-pyrazolone, pyrazole, triazole, oxazolone, isooxazolone, barbituric acid, pyridone, pyridine, rhodanine, pyrazolydinedione, pyrazolopyridone, Meldrum's acid, and fused heterocycles each including any of these heterocycles and, fused thereto, an aromatic hydrocarbon ring or a heterocycle.

Examples of α-aminocarboxylic acids for constituting such poly(amino acid)s include alanine, valine, leucine, phenylalanine, proline, glutamic acid, and aspartic acid. Examples of constituent materials for the poly(amino acid)s further include amino acid derivatives such as benzyl aspartate, methyl glutamate, benzyl glutamate, carbobenzoxylysine, carbobenzoxyornithine, acetyltyrosine, and benzylserine.

In formula (II), n is preferably 100 or less, more preferably 10 to 40.

It is preferable that the amount of the poly(amino acid) to be fixed to the core/shell particles should be 1.0 to 25 parts by weight per 100 parts by weight of the separating agent.

For fixing the poly(amino acid) in a core/shell particulate state by physical adsorption, use can be made of a method in which the core/shell particles are immersed in a solution of the poly (amino acid) (for example, dimethylformamide or dioxane is used as the solvent) and the solvent is thereafter distilled off. Thus, the fixing is accomplished.

1-(4) Polyamides

Examples of the optically active polymer for use in the separating agent of the invention include polyamides. The polyamide has one optically active amino acid residue in the main chain of each repeating unit.

As monomer ingredients for synthesizing the optically active polyamide, an N-substituted amino acid which is an optically active dicarboxylic acid and a diamine were adopted. As the N-substituted amino acid, use can be made of, for example, an N-substituted glutamic acid or an N-substituted aspartic acid. As the diamine, use can be made of an aromatic diamine such as 4,4'-diaminodiphenylmethane or 1,3-phenylenediamine.

One example of methods for synthesizing the polyamide is explained. The polyamide can be synthesized, as stated above, by polymerizing an N-substituted amino acid which is an optically active dicarboxylic acid with a diamine. Specifically, N-methylpyrrolidone (hereinafter, abbreviated to "NMP") is mixed with pyridine (hereinafter, abbreviated to "Py") in a volume ratio of, for example, 4:1. To the resultant liquid is added lithium chloride (hereinafter, abbreviated to "LiCl") in an amount of, for example, 4 wt %. To, for example, 7.5 cm³ of the resultant liquid (hereinafter, referred to as "NMP-Py mixture solution") are added a given amount, for example, 3 mmol, of benzoyl-L-glutamic acid (N-substituted amino acid which is an optically active dicarboxylic acid), an amount equimolar therewith, for example, 3 mmol, of 4,4'-diaminodiphenylmethane (diamine), and a molar amount which is twice the amount of each, for example, 6 mmol, of triphenyl phosphite. The mixture is heated with stirring at a given temperature, e.g., 80° C. for a given period, e.g., 3 hours. After completion of the reaction, the reaction product is added dropwise to methanol, and the resultant mixture is filtered to obtain a polymer, which is vacuum-dried.

Since this polyamide was synthesized using an N-substituted amino acid which is an optically active dicarboxylic acid, the polymer has portions therein which recognize an optical active D- or L-isomer. Optical resolution can be performed based on these portions.

Besides the polyamide described above, examples of polyamides usable as the polyamide according to the invention include ones represented by the following general formula (III) or (IV).

[Chem. 3]

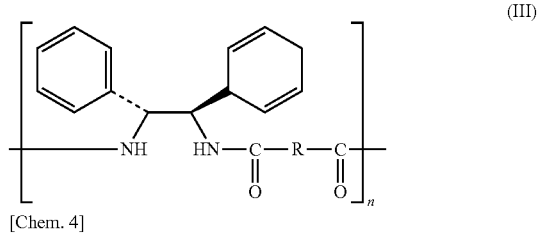

(III)

[Chem. 4]

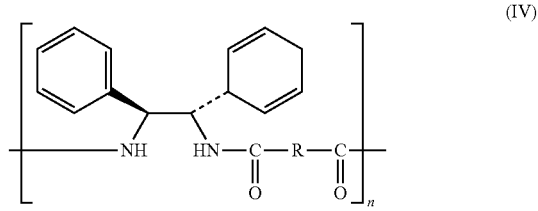

(IV)

In formulae (III) and (IV), R is one or more groups selected from alkylene groups having 2-20 carbon atoms and optionally having a branched structure, groups having one or more aromatic groups having 6-10 carbon atoms, and groups having one or more alicyclic groups having 3-10 carbon atoms. Symbol n is an integer of 50 to 100,000.

The polyamides represented by formulae (III) and (IV) are obtained by the method described in Japanese Examined Patent Publication No. H4-77737. The polyamides can be easily obtained by the reaction of (+)- or (−)-trans-stilbenediamine with the corresponding dicarboxylic acid or a derivative thereof as starting materials.

As the dicarboxylic acid, one represented by HOOC—$R_1$—COOH can be used. Examples of $R_1$ include alkylene groups having 4, 6, 8, or 10 carbon atoms, a phenylene group, an oxydiphenylene group, and cycloalkylene groups having the structure of a cycloalkane, such as cyclohexane or cyclobutane.

Methods for synthesizing the polyamides according to the invention are not limited to the methods described above, and the polyamides may be synthesized by any method other than those. The suitable reaction temperature and reaction time vary depending on reagents used in the reaction and the amounts thereof. The reaction time, reaction temperature, and reagent amounts shown above are examples of conditions under which the optically active polymer according to the invention can be obtained, and can be modified as appropriate.

It is preferable that the amount of the polyamide to be fixed to the core/shell particles should be 1.0 to 25 parts by weight per 100 parts by weight of the separating agent.

For fixing the polyamide on a core/shell particle by physical adsorption, use can be made of a method in which the core/shell particles are immersed in a solution of the polyamide (for example, hexafluoroisopropanol, dimethylformamide, or dichloromethane is used as the solvent) and the solvent is thereafter distilled off. Thus, the fixing is accomplished.

2. Optically Inactive Polyester

Examples of the ligand for use in the invention include an optically inactive polyester. Examples of such polyester include, as polyester, poly(ethylene terephthalate), poly(butylene terephthalate), polyethylene/poly(butylene terephthalate), poly(trimethylene terephthalate), poly(ethylene naphthalate), poly(butylene naphthalate), poly(lactic acid), poly(glycolic acid), poly(8-caprolactone), and poly(oxycarbonyloxy-1,4-phenylene/2,2-isopropylidene-1,4-phenylene) (polycarbonate of bisphenol A). It is preferred to use poly(ethylene terephthalate), poly(butylene terephthalate), poly(lactic acid), or poly(glycolic acid) thereamong.

The weight-average molecular weight of such a polyester is preferably 10,000 to 1,000,000, more preferably 20,000 to 200,000, from the standpoints of tenacious physical adsorption onto the support and ease of handling due to an increase in the viscosity of a solvent for polymer dissolution.

It is preferable that the amount of the polyester to be fixed to the core/shell particles should be 1.0 to 25 parts by weight per 100 parts by weight of the separating agent.

For fixing the polyester in a core/shell particulate state by physical adsorption, use can be made of a method in which the core/shell particles are immersed in a solution of the polyester and the solvent is thereafter distilled off. Thus, the fixing is accomplished.

The separating agent thus obtained is expected to be used for separating high-molecular-weight molecules such as proteins.

3. Protein

A protein can be used as the ligand of the separating agent of the invention. Examples of the protein usable in the invention include substances having a molecular weight of 3 to 300 kDa, preferably 30 to 150 kDa, and having an affinity for a protein to be separated, such as, for example, an antibody.

Preferred of these, for use as the ligand, are protein A, protein G, protein L, and functional mutants thereof, because these proteins attain high selectivity when used in separating antibody proteins.

In cases when separation of an antibody is the main purpose, the ligand is preferably a substance capable of specifically combining with part of immunoglobulin.

The term "functional mutant" means a protein which has at least one modification in the natural amino acid sequence and which still retains at least one of the functions that accompany the natural sequence. Natural sequences include amino acid sequences that spontaneously arise. Examples of changes in amino acids include replacement of one or more amino acids with different amino acids, elimination of one or more amino acids and/or addition of one or more amino acids, or combinations of any of these. Examples thereof further include combinations of addition, elimination, and replacement to be conducted on a natural sequence. The functional mutants may contain a fragment or domain of a protein. The amino acid sequence of each functional mutant may be identical with the natural amino acid sequence to a degree of at least 70%, at least 75%, at least 80%, at least 85%, at least 90%, at least 95%, or at least 98%, and the functional mutant still retains at least one of the functions which accompany the natural sequence.

It is preferable that the amount of the protein to be fixed to the core/shell particles should be 1.0 to 25 parts by weight per 100 parts by weight of the separating agent.

Examples of methods for fixing the protein to the core/shell particles by physical adsorption include a method in which the core/shell particles are immersed in a solution obtained by dissolving the protein in an appropriate solvent, e.g., hexane or chloroform, and thereafter the solvent is distilled off by vacuum drying, etc.

4. Nucleic Acid

A nucleic acid can be used as the ligand of the separating agent of the invention. Such nucleic acid is not particularly limited, and examples thereof include DNA, RNA, oligonucleotides, and modified oligonucleotides. Derivatives of DNA and RNA can also be used. Although the DNA and the RNA may be of the natural or artificial type, it is preferred to use the artificial type which is structurally stable, when the stability of the separating agent is taken into account. In the artificial type, a sequence which does not exist in the natural type can be formed.

Examples of such nucleic acids include ones in which the number of bases is 5 to 10,000.

The number of bases of the artificial-type nucleic acids is preferably about 50 to 200 thereamong. From the standpoint of enabling efficient synthesis, it is preferred to use an artificial nucleic acid having about 100 bases. It is preferable that the artificial-type nucleic acids should have no adjoining thymine bases from the standpoint of preventing dimerization of thymine.

Furthermore, the nucleic acids may have been derivatized with a protective group in view of the durability of the separating agent. Specifically, the hydroxy group(s) at the 5'-position and/or the 3'-position can be derivatized using a phosphoric ester group, acyl group, alkoxycarbonyl group, benzyl group, substituted benzyl group, allyl group, etc.

It is preferable that the amount of the nucleic acid to be fixed to the core/shell particles should be 1.0 to 25 parts by weight per 100 parts by weight of the separating agent. In case where the amount of the nucleic acid fixed is less than 1.0 part by weight per 100 parts by weight of the separating agent, the nucleic acid cannot be made to present stably in the separating agent, resulting in insufficient separation performance. Meanwhile, in case where the amount of the nucleic acid fixed exceeds 25 parts by weight, per 100 parts by weight of the separating agent, the nucleic acid cannot be wholly fixed to the core/shell particles and partly remains free, resulting in the possibility of adversely affecting the separation performance.

For fixing the nucleic acid to the core/shell particles, use may be made of, for example, a method in which the core/shell particles are dispersed in distilled water to give a suspension, either the nucleic acid as such or an aqueous solution obtained by dissolving the nucleic acid in distilled water is added to the suspension, and the mixture is dried. In this method, the nucleic acid may be added in such a manner that some of the nucleic acid is added not as an aqueous solution but as it is and the remainder thereof is added in the form of an aqueous solution.

The separating agent of the invention can be used as a separating agent for optical isomers in the case where the ligand used is optically active, and can be used as a separating agent for affinity chromatography in the case where the ligand used is optically inactive. Besides being used as packing materials for liquid chromatography, these separating agents can be used as packing materials for supercritical liquid chromatography, gas chromatography, electrophoresis, and as packing materials of capillary column in capillary electrochromatography (CEC), CZE (capillary zone electrophoresis), or MEKC (micellar electrokinetic chromatography).

EXAMPLES

The invention will be explained in detail by reference to Examples, but the invention should not be construed as being limited to these Examples. Incidentally, the number of theoretical plates (N), retention factor (k'), and separation factor (α) in the following Examples are defined by the following equations.

<Number of Theoretical Plates>

$N = 16 \times [(\text{retention time})/(\text{peak width})]^2$

<Retention Factor>

$k' = [(\text{retention time of target substance}) - (\text{dead time})] / (\text{dead time})$ <Separation Factor>

α = (retention factor of target substance which is held more strongly)/(retention factor of target substance which is held more weakly)

The elution time of tri-tert-butylbenzene was taken as the dead time.

Example 1

Process for Producing Packing Material Containing 5 wt % Cellulose Tris(4-chloro-3-methylphenylcarbamate) Fixed by Physical Adsorption, and Process for Producing Packed Column (1) Synthesis of Cellulose Tris (4-chloro-3-methylphenylcarbamate) (1)

Commercial 4-chloro-3-methylphenyl isocyanate was reacted with cellulose in a pyridine solvent to obtain a white solid (1).

Reaction conditions were set with reference to the statement in non-patent document 2.

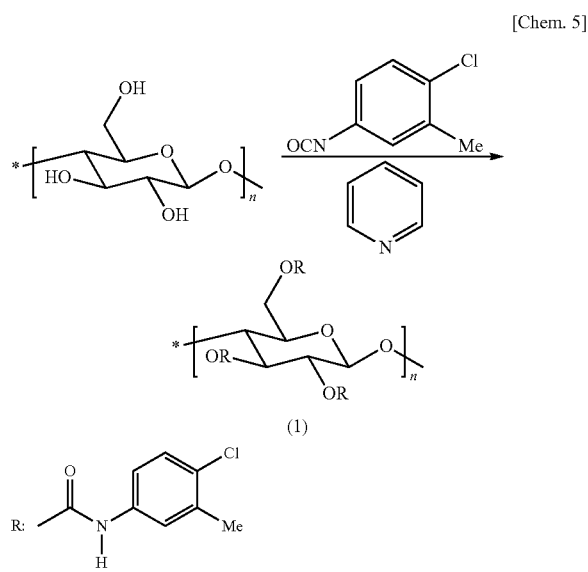

[Chem. 5]

(2) Production of Packing Material Containing 5 wt % Fixed Cellulose Tris(4-chloro-3-methylphenylcarbamate) (1)

In 30 mL of tetrahydrofuran was dissolved 0.2 g of the cellulose derivative (1) obtained in (1). To this solution was added 3.8 g of core/shell type silica gel (obtained by taking the packing material out of a special column (4.6×150 mm) manufactured by ChromaNik Technologies Inc. (particle diameter, 2.6 μm; pore diameter, 30 nm; core shell C4), heating the packing material to 600 degrees C. over 1 hour in an electric furnace, thereafter keeping the temperature for 5 hours, allowing the packing material to cool, then dispersing the packing material in 4-N hydrochloric acid, stirring the dispersion overnight, washing the packing material with pure water, and then drying the packing material; particle diameter, 2.6 μm; pore diameter, 30 nm (catalog value); core diameter, 1.6 μm; material of the cores, glass; thickness of the shells, 0.5 μm; material of the shells, silica gel (hydrolyzate of polyalkoxysiloxane)). The mixture was stirred by shaking for several minutes, and thereafter the solvent was distilled off under vacuum. Thus, a packing material to which cellulose tris(4-chloro-3-methylphenylcarbamate) (1) had been fixed in an amount of 5 wt % was produced.

(3) Production of Column Packed with Packing Material Containing 5 wt % Fixed Cellulose Tris(4-chloro-3-methylphenylcarbamate) (1)

The fixed-ligand packing material produced in (2) was packed with pressurization into a stainless-steel column having dimensions of 0.46 cm (diameter)×25 cm (length) by a slurry filling method. Thus, a column was produced.

Example 2

Process for Producing Packing Material Containing 2.1 wt % Fixed Cellulose Tris(3,5-dimethylphenylcarbamate), and Process for Producing Packed Column (4) Synthesis of Cellulose Tris(3,5-dimethylphenylcarbamate) (2)

Commercial 3,5-dimethylphenyl isocyanate was reacted with cellulose in a pyridine solvent to obtain a white solid (2). Reaction conditions were set with reference to non-patent documents 3 and 4.

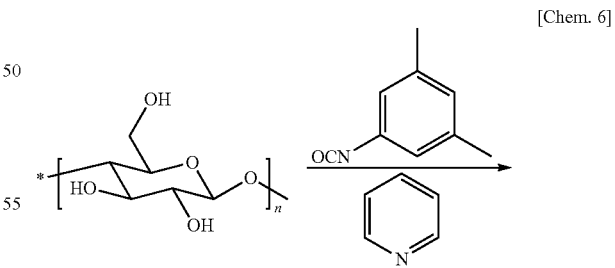

[Chem. 6]

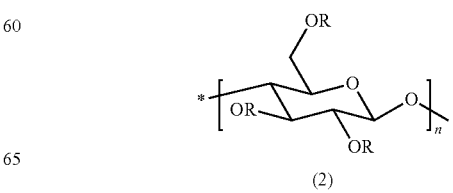

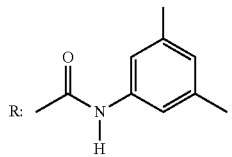

(5) Production of Packing Material Containing 2.1 wt % Fixed Cellulose Tris(3,5-dimethylphenylcarbamate) (2)

In 34 mL of tetrahydrofuran was dissolved 0.1 g of the cellulose derivative (2) obtained in (4). To this solution was added 4.0 g of core/shell type silica gel (obtained by taking the packing material out of a special column (4.6×150 mm) manufactured by ChromaNik Technologies Inc. (particle diameter, 2.6 μm; pore diameter, 30 nm; core shell C4), heating the packing material to 600 degrees C. over 1 hour in an electric furnace, thereafter keeping the temperature for 5 hours, allowing the packing material to cool, then dispersing the packing material in 4-N hydrochloric acid, stirring the dispersion overnight, washing the packing material with pure water, and then drying the packing material; particle diameter, 2.6 μm; pore diameter, 30 nm (catalog value); core diameter, 1.6 μm; material of the cores, glass; thickness of the shells, 0.5 μm; material of the shells, silica gel (hydrolyzate of polyalkoxysiloxane)). The mixture was stirred by shaking, and thereafter the solvent was distilled off under vacuum. Thus, a packing material to which cellulose tris(3,5-dimethylphenylcarbamate) (2) had been fixed in an amount of 2.1 wt % was produced.

(6) Production of Column Packed with Packing Material Containing 2.1 wt % Fixed Cellulose Tris(3,5-dimethylphenylcarbamate) (2)

The fixed-ligand packing material produced in (5) was packed with pressurization into a stainless-steel column having dimensions of 0.46 cm (diameter)×15 cm (length) by a slurry filling method. Thus, a column was produced.

Example 3

Process for Producing Packing Material Containing 7.6 wt % Fixed Cellulose Tris(3,5-dimethylphenylcarbamate), and Process for Producing Packed Column

(7) Production of Packing Material Containing 7.6 wt % Fixed Cellulose Tris(3,5-dimethylphenylcarbamate) (2)

In 34 mL of tetrahydrofuran was dissolved 0.33 g of the cellulose derivative (2) obtained in (4). To this solution was added 4.0 g of core/shell type silica gel (obtained by taking the packing material out of a special column (4.6×150 mm) manufactured by ChromaNik Technologies Inc. (particle diameter, 2.6 μm; pore diameter, 30 nm; core shell C4), heating the packing material to 600 degrees C. over 1 hour in an electric furnace, thereafter keeping the temperature for 5 hours, allowing the packing material to cool, then dispersing the packing material in 4-N hydrochloric acid, stirring the dispersion overnight, washing the packing material with pure water, and then drying the packing material; particle diameter, 2.6 μm; pore diameter, 30 nm (catalog value); core diameter, 1.6 μm; material of the cores, glass; thickness of the shells, 0.5 μm; material of the shells, silica gel (hydrolyzate of polyalkoxysiloxane)). The mixture was stirred by shaking for several minutes, and thereafter the solvent was distilled off under vacuum. Thus, a packing material to which cellulose tris(3,5-dimethylphenylcarbamate) (2) had been fixed in an amount of 7.6 wt % was produced.

(8) Production of Column Packed with Packing Material Containing 7.6 wt % Fixed Cellulose Tris (3,5-dimethylphenylcarbamate) (2)

The fixed-ligand packing material produced in (7) was packed with pressurization into a stainless-steel column having dimensions of 0.46 cm (diameter)×15 cm (length) by a slurry filling method. Thus, a column was produced.

Example 4

Process for Producing Packing Material Containing 5 wt % Amylose Tris (3-chloro-4-methylphenylcarbamate) Fixed by Physical Adsorption, and Process for Producing Packed Column

(9) Synthesis of Amylase Tris(3-chloro-4-methylphenylcarbamate) (3)

Commercial 3-chloro-4-methylphenyl isocyanate was reacted with amylose in a pyridine solvent to obtain a white solid (3). Reaction conditions were set with reference to non-patent document 5.

[Chem. 7]

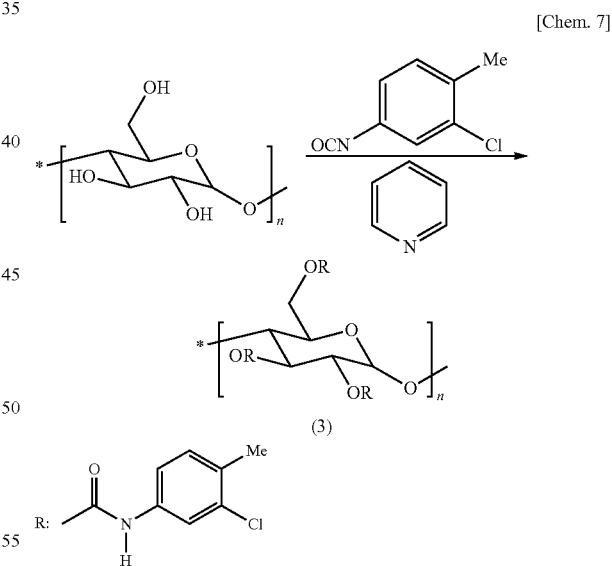

(10) Production of Packing Material Containing 5 wt % Fixed Amylose Tris(3-chloro-4-methylphenylcarbamate) (3)

In 15 mL of tetrahydrofuran was dissolved 0.1 g of the amylose derivative (3) obtained in (9). To this solution was added 1.8 g of core/shell type silica gel (obtained by taking the packing material out of a special column (4.6×150 mm) manufactured by ChromaNik Technologies Inc. (particle diameter, 2.6 μm; pore diameter, 30 nm; core shell), heating the packing material to 600 degrees C. over 1 hour in an electric furnace, thereafter keeping the temperature for 5 hours, allowing the packing material to cool, then dispersing the packing material in 4-N hydrochloric acid, stirring the dispersion overnight, washing the packing material with pure water, and then drying the packing material; particle diameter, 2.6 μm; pore diameter, 30 nm (catalog value); core diameter, 1.6 μm; material of the cores, glass; thickness of the shells, 0.5 μm; material of the shells, silica gel (hydrolyzate of polyalkoxysiloxane)). The mixture was stirred by shaking for several minutes, and thereafter the solvent was distilled off under vacuum. Thus, a packing material to which amylose tris(3-chloro-4-methylphenylcarbamate) (3) had been fixed in an amount of 5 wt % was produced.

(11) Production of Column Packed with Packing Material Containing 5 wt % Fixed Amylose Tris(3-chloro-4-methylphenylcarbamate) (3)

The fixed-ligand packing material produced in (10) was packed with pressurization into a stainless-steel column having dimensions of 0.21 cm (diameter)×15 cm (length) by a slurry filling method. Thus, a column was produced.

Example 5

Process for Producing Packing Material Containing 5 wt % Fixed Amylose Tris(3,5-dimethylphenylcarbamate), and Process for Producing Packed Column

(12) Synthesis of Amylose Tris(3,5-dimethylphenylcarbamate) (4)

Commercial 3,5-dimethylphenyl isocyanate was reacted with amylose in a pyridine solvent to obtain a white solid (4). Reaction conditions were set with reference to non-patent document 6.

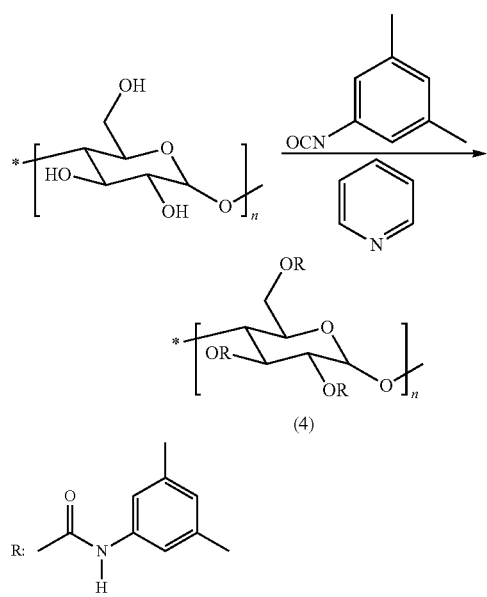

[Chem. 8]

(13) Production of Packing Material Containing 5 wt % Fixed Amylose Tris(3,5-dimethylphenylcarbamate) (4)

In 15 mL of ethyl acetate was dissolved 0.1 g of the amylose derivative (4) obtained in (12). To this solution was added 1.9 g of core/shell type silica gel (obtained by taking the packing material out of a special column (4.6×150 mm) manufactured by ChromaNik Technologies Inc. (particle diameter, 2.6 μm; pore diameter, 30 nm; core shell), heating the packing material to 600 degrees C. over 1 hour in an electric furnace, thereafter keeping the temperature for 5 hours, allowing the packing material to cool, then dispersing the packing material in 4-N hydrochloric acid, stirring the dispersion overnight, washing the packing material with pure water, and then drying the packing material; particle diameter, 2.6 μm; pore diameter, 30 nm (catalog value); core diameter, 1.6 μm; material of the cores, glass; thickness of the shells, 0.5 μm; material of the shells, silica gel (hydrolyzate of polyalkoxysiloxane)). The mixture was stirred by shaking, and thereafter the solvent was distilled off under vacuum. Thus, a packing material to which amylose tris(3,5-dimethylphenylcarbamate) (4) had been fixed in an amount of 5 wt % was produced.

(14) Production of Column Packed with Packing Material Containing 5 wt % Fixed Amylose Tris(3,5-dimethylphenylcarbamate) (4)

The fixed-ligand packing material produced in (13) was packed with pressurization into a stainless-steel column having dimensions of 0.21 cm (diameter)×15 cm (length) by a slurry filling method. Thus, a column was produced.

Example 6

Process for Producing Packing Material Containing 5 wt % Fixed Optically Active Polyamide (5), and Process for Producing Packed Column

(15) Synthesis of Optically Active Polyamide (5)

Commercial (1S,2S)-(−)-1,2-diphenylethylenediamine was reacted with adipoyl chloride in a solution mixture of triethyamine and dimethylacetamide to obtain a white solid (5). Reaction conditions were set with reference to patent document 11.

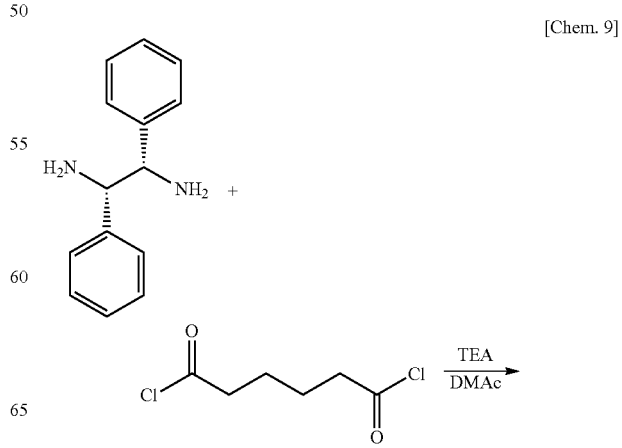

[Chem. 9]

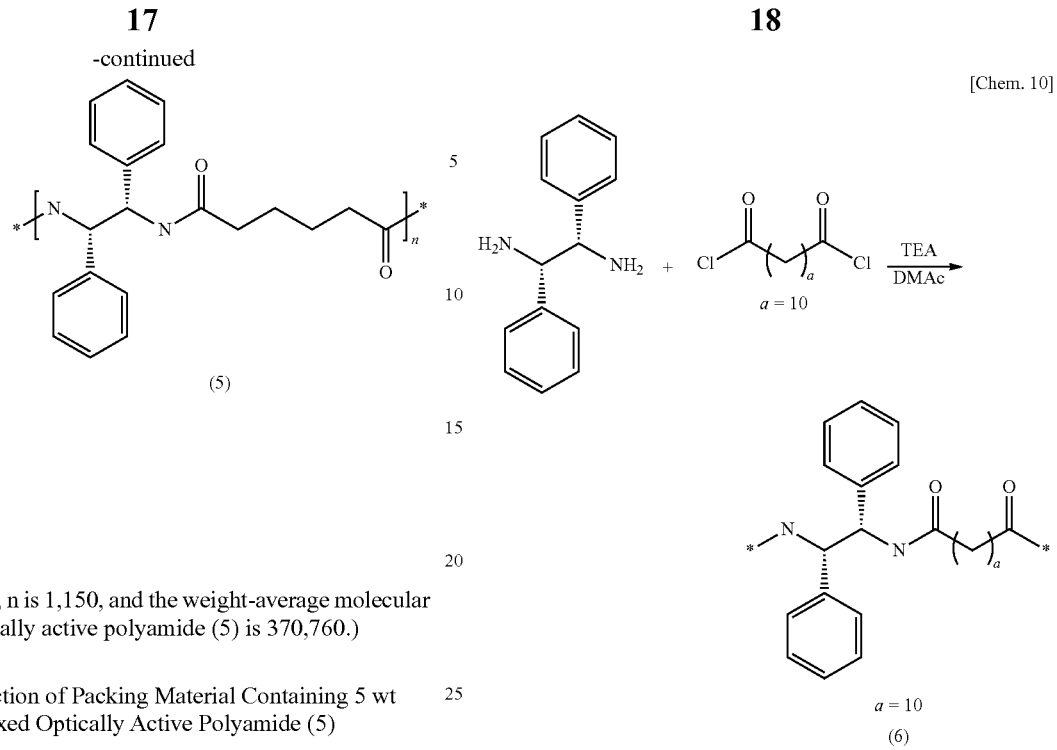

(In formula (5), n is 1,150, and the weight-average molecular weight of optically active polyamide (5) is 370,760.)

(16) Production of Packing Material Containing 5 wt % Fixed Optically Active Polyamide (5)

To 1.27 g of core/shell type silica gel (manufactured by Advanced Materials Technology (AMT), INC.; particle diameter, 3.4 μm; pore diameter, 40 nm (catalog value), core diameter, 3.4 μm; material of the cores, glass; thickness of the shells, 0.5 μm; material of the shells, silica gel (hydrolyzate of polyalkoxysiloxane)) was added 1.5 mL of a hexafluoroisopropyl alcohol solution containing 0.07 g of the optically active polyamide (5) obtained in (15). Thereafter, the hexafluoroisopropyl alcohol was distilled off. The obtained residue was washed with methanol to produce a packing material to which the optically active polyamide (5) had been fixed in an amount of 5 wt %.

(17) Production of Column Packed with Packing Material Containing 5 wt % Fixed Optically Active Polyamide (5)

The fixed-ligand packing material produced in (16) was packed with pressurization into a stainless-steel column having dimensions of 0.21 cm (diameter)×15 cm (length) by a slurry filling method. Thus, a column was produced.

Example 7

Process for Producing Packing Material Containing 5 wt % Fixed Optically Active Polyamide (6), and Process for Producing Packed Column

(18) Synthesis of Optically Active Polyamide (6)

Commercial (1S,2S)-(−)-1,2-diphenylethylenediamine was reacted with dodecanedioyl dichloride in a solution mixture of triethyamine and dimethylacetamide to obtain a white solid (6). Reaction conditions were set with reference to patent document 11.

(In formula (5), n is 8,624, and the weight-average molecular weight of optically active polyamide (6) is 3,506,151.)

(19) Production of Packing Material Containing 5 wt % Fixed Optically Active Polyamide (6)

To 1.28 g of core/shell type silica gel (manufactured by Advanced Materials Technology (AMT), INC.; particle diameter, 3.4 μm; pore diameter, 40 nm (catalog value), core diameter, 3.4 μm; material of the cores, glass; thickness of the shells, 0.5 μm; material of the shells, silica gel (hydrolyzate of polyalkoxysiloxane)) was added 1.5 mL of a hexafluoroisopropyl alcohol solution containing 0.07 g of the optically active polyamide (6) obtained in (18). Thereafter, the hexafluoroisopropyl alcohol was distilled off. The obtained residue was washed with methanol to produce a packing material to which the optically active polyamide (6) had been fixed in an amount of 5 wt %.

(20) Production of Column Packed with Packing Material Containing 5 wt % Fixed Optically Active Polyamide (6)

The fixed-ligand packing material produced in (19) was packed with pressurization into a stainless-steel column having dimensions of 0.21 cm (diameter)×15 cm (length) by a slurry filling method. Thus, a column was produced.

Example 8

Process for Producing Packing Material Containing 5 wt % Fixed Poly(β-benzyl L-aspartate) (7), and Process for Producing Packed Column

(21) Production of Packing Material Containing 5 wt % Fixed Poly(β-benzyl L-aspartate) (7)

To 1.28 g of core/shell type silica gel (manufactured by Advanced Materials Technology (AMT), INC.; particle diameter, 3.4 µm; pore diameter, 40 nm (catalog value), core diameter, 3.4 µm; material of the cores, glass; thickness of the shells, 0.5 µm; material of the shells, silica gel (hydrolyzate of polyalkoxysiloxane)) was added 1 mL of a dichloromethane solution containing 0.07 g of poly(β-benzyl L-aspartate) (7) (manufactured by Sigma-Aldrich Co. LLC; weight-average molecular weight, 15,000-50,000). Thereafter, the dichloromethane was distilled off. The obtained residue was washed with methanol to produce a packing material to which poly (β-benzyl L-aspartate) (7) had been fixed in an amount of 5 wt %.

(22) Production of Column Packed with Packing Material Containing 5 wt % Fixed Poly(β-benzyl L-aspartate) (7)

The fixed-ligand packing material produced in (21) was packed with pressurization into a stainless-steel column having dimensions of 0.21 cm (diameter)×15 cm (length) by a slurry filling method. Thus, a column was produced.

Example 9

Process for Producing Packing Material Containing 5 wt % Fixed Poly(butylene terephthalate), and Process for Producing Packed Column

(23) Production of Packing Material Containing 5 wt % Fixed Poly(butylene terephthalate) (8)

To 1.9 g of core/shell type silica gel (obtained by taking the packing material out of a special column (4.6×150 mm) manufactured by ChromaNik Technologies Inc. (particle diameter, 2.6 µm; pore diameter, 30 nm; core shell), heating the packing material to 600 degrees C. over 1 hour in an electric furnace, thereafter keeping the temperature for 5 hours, allowing the packing material to cool, then dispersing the packing material in 4-N hydrochloric acid, stirring the dispersion overnight, washing the packing material with pure water, and then drying the packing material; particle diameter, 2.6 µm; pore diameter, 30 nm (catalog value); core diameter, 1.6 µm; material of the cores, glass; thickness of the shells, 0.5 µm; material of the shells, silica gel (hydrolyzate of polyalkoxysiloxane)) was added 2 mL of a hexafluoroisopropyl alcohol solution containing 0.1 g of poly(butylene terephthalate) (Duranex 300FP) (8). Thereafter, the hexafluoroisopropyl alcohol was distilled off. The obtained residue was washed with methanol to produce a packing material to which polybutylene terephthalate) (8) had been fixed in an amount of 5 wt %.

(24) Production of Column Packed with Packing Material Containing 5 wt % Fixed Poly(butylene terephthalate) (8)

The fixed-ligand packing material produced in (23) was packed with pressurization into a stainless-steel column having dimensions of 0.21 cm (diameter)×15 cm (length) by a slurry filling method. Thus, a column was produced.

Example 10

Process for Producing Packing Material Containing 5 wt % Fixed Poly(ethylene terephthalate), and Process for Producing Packed Column

(24) Production of Packing Material Containing 5 wt % Fixed Poly(ethylene terephthalate) (9)

To 1.4 g of core/shell type silica gel (obtained by taking the packing material out of a special column (4.6×150 mm) manufactured by ChromaNik Technologies Inc. (particle diameter, 2.6 µm; pore diameter, 30 nm; core shell), heating the packing material to 600 degrees C. over 1 hour in an electric furnace, thereafter keeping the temperature for 5 hours, allowing the packing material to cool, then dispersing the packing material in 4-N hydrochloric acid, stirring the dispersion overnight, washing the packing material with pure water, and then drying the packing material; particle diameter, 2.6 µm; pore diameter, 30 nm (catalog value); core diameter, 1.6 µm; material of the cores, glass; thickness of the shells, 0.5 µm; material of the shells, silica gel (hydrolyzate of polyalkoxysiloxane)) was added 4 mL of a hexafluoroisopropyl alcohol/dichloromethane (1:1) mixture solution containing 0.07 g of poly(ethylene terephthalate) (TR8550FF, manufactured by Teijin Chemicals Ltd.) (9). Thereafter, the hexafluoroisopropyl alcohol and the dichloromethane were distilled off. The obtained residue was washed with methanol to produce a packing material to which poly(ethylene terephthalate) (9) had been fixed in an amount of 5 wt %.

(25) Production of Column Packed with Packing Material Containing 5 wt % Fixed Poly(ethylene terephthalate) (9)

The fixed-ligand packing material produced in (24) was packed with pressurization into a stainless-steel column having dimensions of 0.21 cm (diameter)×15 cm (length) by a slurry filling method. Thus, a column was produced.

Example 11

Process for Producing Packing Material Containing 5 wt % Fixed Poly(lactic acid), and Process for Producing Packed Column

(26) Production of Packing Material Containing 5 wt % Fixed Poly(lactic acid) (10)

To 1.48 g of core/shell type silica gel (manufactured by Advanced Materials Technology (AMT), INC.; particle diameter, 3.4 µm; pore diameter, 40 nm (catalog value), core diameter, 3.4 µm; material of the cores, glass; thickness of the shells, 0.5 µm; material of the shells, silica gel (hydrolyzate of polyalkoxysiloxane)) was added 1 mL of a hexafluoroisopropyl alcohol solution containing 0.08 g of poly(lactic acid) (manufactured by Polysciences Inc.; Poly(D,L-lactic acid); Mw, 6,000-16,000) (10). Thereafter, the hexafluoroisopropyl alcohol was distilled off. The obtained residue was washed with methanol to produce a packing material to which poly (lactic acid) (10) had been fixed in an amount of 5 wt %.

(27) Production of Column Packed with Packing Material Containing 5 wt % Fixed Poly(lactic acid) (10)

The fixed-ligand packing material produced in (26) was packed with pressurization into a stainless-steel column having dimensions of 0.21 cm (diameter)×15 cm (length) by a slurry filling method. Thus, a column was produced.

Application Example 1

The optical-isomer separation column produced in Example 1 was evaluated for column performance (N value) by liquid chromatography using the compound having the following structural formula. Shown for comparison was the column performance (N value) of a column packed with the packing material of non-patent document 1, which contained core/shell type silica gel (particle diameter, 2.6 μm; opening size, 9 nm) and cellulose tris(4-chloro-3-methylphenylcarbamate) (1) fixed thereto. The evaluation conditions for both the column of Example 1 and that described in the document were as follows. As the mobile phase was used n-hexane/2-propanol=90/10. The flow rate and the temperature were set at 1.0 mL/min and 25° C., respectively.

TABLE 1

Performances (N values) of the columns of Example 1 and document

| Racemate | Separating agent | |
|---|---|---|
| | Example 1 | Value of document (non-patent document 1) |
| trans-Stylbene oxide | N1 = 20,625 N2 = 19,343 | N1 = 16,160 N2 = 11,663 |

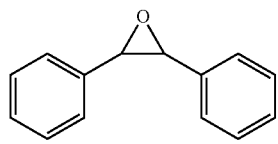

[Chem. 11]

Structure of Trans-Stylbene Oxide

Application Example 2

The optical-isomer separation columns produced in Example 2 and Example 3 were evaluated for column performances (k' value, α value, and N value) by liquid chromatography using trans-stylbene oxide, which was shown above.

Shown for comparison were the column performances (k' value, α value, and N value) of an optical-isomer separation column packed with a packing material obtained by fixing cellulose tris(3,5-dimethylphenylcarbamate) (2) to wholly porous type silica gel (particle diameter, 5 μm; pore diameter, 12 nm) in an amount of 2.1 wt % by the method described in Example 2. The evaluation conditions for all of the columns of Examples 2 and 3 and Comparative Example were as follows. As the mobile phase was used n-hexane/2-propanol=90/10. The flow rate and the temperature were set at 1.0 mL/min and 25° C., respectively.

TABLE 2

Performances (k' value, α value, and N value) of the columns of Examples 2 and 3 and document

| Racemate | Separating agent | | |
|---|---|---|---|
| | Example 2 Core/shell, 2.1 wt % fixed | Example 3 Core/shell, 7.6 wt % fixed | Comparative Example Wholly porous, 2.1 wt % fixed |
| trans-Stylbene oxide | k1' = 0.133 α = 2.335 N1 = 10,781 N2 = 11,593 | k1' = 0.497 α = 2.165 N1 = 2,193 N2 = 2,111 | k1' = 0.213 α = 1.490 N1 = 12,690 N2 = 13,422 |

Application Example 3

The optical-isomer separation columns produced in Example 4 and Example 5 were evaluated for column performances (k' value and α value) by liquid chromatography using trans-stylbene oxide, which was shown above. Shown for comparison were the column performances (k' value and α value) of an optical-isomer separation column packed with a packing material obtained by fixing amylose tris(3-chloro-4-methylphenylcarbamate) (3) to wholly porous type silica gel (particle diameter, 5 μm; pore diameter, 12 nm) in an amount of 5.0 wt % by the method described in Example 4. The evaluation conditions for all of the columns of Example 3, Example 4, and Comparative Example were as follows. As the mobile phase was used n-hexane/2-propanol=90/10. The flow rate and the temperature were set at 0.15 mL/min and 25° C., respectively.

TABLE 3

Performances (k' value and α value) of the columns of Examples 4 and 5 and Comparative Example

| Racemate | Separating agent | | |
|---|---|---|---|
| | Example 4 Core/shell, 5.0 wt % fixed | Example 5 Core/shell, 5.0 wt % fixed | Comparative Example Wholly porous, 5.0 wt % fixed |
| trans-Stylbene oxide | k1' = 0.304 α = 1.45 | k1' = 0.639 α = 2.97 | k1' = 0.282 α = 1.24 |

Application Example 4

The optical-isomer separation columns produced in Example 6 and Example 7 were evaluated for column performances (k' value and α value) by liquid chromatography using trans-stylbene oxide, which was shown above. Shown for comparison were the column performances (k' value and α value) of an optical-isomer separation column packed with a packing material obtained by fixing an optically active polyamide (5) to wholly porous type silica gel (particle diameter, 5 μm; pore diameter, 12 nm) in an amount of 5.0 wt % by the method described in Example 6. The evaluation conditions for all of the columns of Example 5, Example 6, and Comparative Example were as follows. As the mobile phase was used n-hexane/2-propanol=90/10. The flow rate and the temperature were set at 0.15 mL/min and 25° C., respectively.

TABLE 4

Performances (k' value and α value) of the columns of Examples 6 and 7 and Comparative Example

| Racemate | Separating agent | | |
|---|---|---|---|
| | Example 6 Core/shell, 5.0 wt % fixed | Example 7 Core/shell, 5.0 wt % fixed | Comparative Example Wholly porous, 5.0 wt % fixed |
| trans-Stylbene oxide | k1' = 0.511 α = 2.11 | k1' = 0.156 α = 1.00 | k1' = 0.220 α = 1.06 |

Application Example 5

The columns produced in Example 9 and Example 10 were evaluated for column performance (t value) by liquid chromatography using o-terphenyl, m-terphenyl, and p-terpheny, which are shown below. Shown for comparison was the column performance (t value) of a column packed with a packing material obtained by fixing poly(butylene terephthalate) (8)

to wholly porous type silica gel (particle diameter, 5 μm; pore diameter, 12 nm) in an amount of 5.0 wt % by the method described in Example 9. The evaluation conditions for all of the columns of Example 9, Example 10, and Comparative Example were as follows. As the mobile phase was used n-hexane. The flow rate and the temperature were set at 0.15 mL/min and 25° C., respectively.

[Chem. 12]

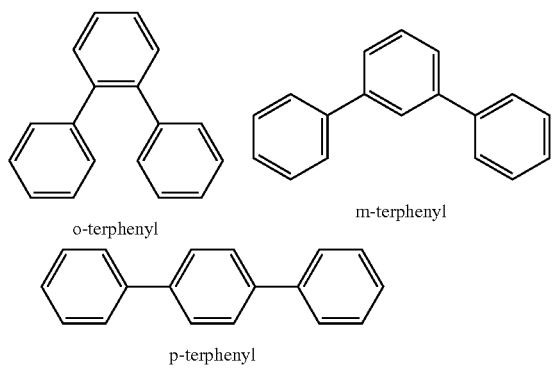

o-terphenyl m-terphenyl p-terphenyl

TABLE 5

Performance (t value) of the columns of
Examples 9 and 10 and Comparative Example

| Compound | Separating agent | | |
|---|---|---|---|
| | Example 9 Core/shell, 5.0 wt % fixed | Example 10 Core/shell, 5.0 wt % fixed | Comparative Example Wholly porous, 5.0 wt % fixed |
| o-Terphenyl | t = 2.904 | t = 2.559 | t = 3.041 |
| m-Terphenyl | t = 3.222 | t = 2.805 | t = 3.156 |
| p-Terphenyl | t = 3.413 | t = 2.805 | t = 3.156 |
| Results of separation | The three compounds were separated | o-Terphenyl only was separated | o-Terphenyl only was separated |

The invention claimed is:

1. A separating agent comprising a support and a ligand fixed to the surface of the support by physical adsorption, wherein the support is core/shell particles each formed of a core constituted of a nonporous inorganic substance and a porous shell, the shell having a pore diameter of 30 nm or larger, the shell being constituted of a hydrolyzate of a polyalkoxysiloxane, and the ligand is an optically active polymer, an optically inactive polyester, a protein, or a nucleic acid.

2. The separating agent according to claim 1, wherein, in the core/shell particles, the cores are constituted of a glass and the thickness ratio of the cores to the shells is from 4:1 to 2:1.

3. The separating agent according to claim 1, wherein the optically active polymer is selected from polysaccharides or derivatives thereof, optically active poly(meth)acrylamides, optically active poly(amino acid)s, and optically active polyamides.

4. The separating agent according to claim 1, wherein the optically active polymer is selected from polysaccharides or derivatives thereof, optically active poly(amino acid)s, and optically active polyamides.

5. The separating agent according to claim 1, wherein the protein is selected from glycoproteins, protein A, protein G, protein L, and functional mutants thereof.

6. The separating agent according to claim 1, wherein the optically inactive polyester is selected from poly(butylene terephthalate), poly(ethylene terephthalate), and poly(lactic acid).

7. The separating agent according to claim 1, wherein the nucleic acid is selected from DNAs and RNAs which each have 5 to 10,000 bases and from derivatives thereof.

8. The separating agent according to claim 1, which is a separating agent for chromatography.

* * * * *